United States Patent
Meyer et al.

(10) Patent No.: US 7,255,735 B2
(45) Date of Patent: Aug. 14, 2007

(54) SURFACE-MODIFIED SILICON DIOXIDE-TITANIUM DIOXIDE MIXED OXIDES

(75) Inventors: Jürgen Meyer, Stockstadt (DE); Kai Schumacher, Hofheim (DE); Steffen Hasenzahl, Morris Plains, NJ (US); Heike Riedemann, Mombris (DE); Ann Gray, Hanau (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/312,534

(22) Filed: Dec. 21, 2005

(65) Prior Publication Data

US 2006/0144296 A1    Jul. 6, 2006

(30) Foreign Application Priority Data

Dec. 23, 2004   (EP)   ................. 04030587

(51) Int. Cl.
| | |
|---|---|
| C09C 3/12 | (2006.01) |
| C09C 1/36 | (2006.01) |
| C09C 1/28 | (2006.01) |
| C08K 5/54 | (2006.01) |
| C01G 23/047 | (2006.01) |
| A61K 8/04 | (2006.01) |
| A61K 8/19 | (2006.01) |
| A61K 8/25 | (2006.01) |
| A61K 8/29 | (2006.01) |
| A61K 8/30 | (2006.01) |

(52) U.S. Cl. ................. 106/445; 106/442; 106/446; 424/59; 427/219; 428/403; 428/405

(58) Field of Classification Search ............... 106/442, 106/445, 446; 424/59; 427/219; 428/403, 428/405
See application file for complete search history.

(56) References Cited

U.S. PATENT DOCUMENTS

| | | | |
|---|---|---|---|
| 5,451,390 A | | 9/1995 | Hartmann et al. |
| 5,762,914 A | * | 6/1998 | Hartmann et al. ............ 424/59 |
| 5,902,569 A | | 5/1999 | Oshima et al. |
| 6,022,404 A | * | 2/2000 | Ettlinger et al. ............ 106/404 |
| 6,534,068 B2 | * | 3/2003 | Hemme et al. ............ 424/400 |
| 6,663,851 B1 | | 12/2003 | Deller et al. |
| 6,773,697 B2 | * | 8/2004 | Hemme et al. ................ 424/65 |
| 2003/0129153 A1 | | 7/2003 | Moerters et al. |
| 2006/0057385 A1 | * | 3/2006 | Schumacher et al. ....... 428/404 |
| 2006/0159635 A1 | * | 7/2006 | Meyer et al. ................. 424/59 |
| 2006/0159637 A1 | * | 7/2006 | Meyer et al. ................. 424/59 |

FOREIGN PATENT DOCUMENTS

| | | |
|---|---|---|
| WO | WO 03/037287 A1 | 5/2003 |
| WO | WO 2004/056927 A2 | 7/2004 |
| WO | WO 2005/110922 A1 | 11/2005 |

OTHER PUBLICATIONS

European Search Report Dated Jun. 14, 2006.

* cited by examiner

*Primary Examiner*—Anthony J. Green
(74) *Attorney, Agent, or Firm*—Michael A. Sanzo; Law Office of Michael A. Sanzo, LLC

(57) ABSTRACT

Pyrogenically prepared surface-modified silicon dioxide-titanium dioxide mixed oxides are prepared by spraying pyrogenically prepared silicon dioxide-titanium dioxide mixed oxides with a surface-modifying agent. The surface-modified pyrogenically prepared silicon dioxide-titanium dioxide mixed oxides can be used in sun protection formulation.

17 Claims, No Drawings

SURFACE-MODIFIED SILICON DIOXIDE-TITANIUM DIOXIDE MIXED OXIDES

CROSS REFERENCE TO RELATED APPLICATIONS

This application claims priority to European Application No. EP 04 030 587.2, filed Dec. 23, 2004, which is incorporated in its entirety herein by reference.

FIELD OF THE INVENTION

The invention relates to pyrogenically prepared, surface-modified silicon dioxide-titanium dioxide mixed oxides, to a process for their preparation and to their use in sun protection formulations.

BACKGROUND OF THE INVENTION

Cosmetic preparations, such as creams or lotions, comprising UV filters are used to protect the skin from too intensive UV radiation. As UV filters these preparations generally comprise one or more organic compounds which absorb in the wavelength range from 290 to 400 nm, which is divided into the ranges: UVB radiation (290 to 320 nm); UVA radiation (320 to 400 nm).

UVB radiation, which is higher-energy, causes the typical symptoms of sunburn and also causes suppression of the immune defence, while UVA radiation, which penetrates more deeply into the layers of the skin, causes premature ageing of the skin. Because the cooperation of the two types of radiation is said to promote the development of skin diseases caused by light, such as skin cancer, there has been a search for possible ways of further improving significantly UV protection.

Metal oxides, such as titanium dioxide or zinc oxide, are widely used in sun protection agents. Their action is based substantially on the reflection, scattering and absorption of the damaging UV radiation and is dependent substantially on the primary particle size of the metal oxides. Microfine titanium dioxide is used in many cosmetic formulations because it is chemically inert and toxicologically harmless and results neither in skin irritations nor sensitisation. Microfine titanium dioxide can be prepared by wet chemical precipitation processes or thermal (pyrogenic) gas-phase processes.

Pyrogenically prepared silicon dioxide-titanium dioxide mixed oxide is known from DE 4235996. A disadvantage of the known pyrogenically prepared silicon dioxide-titanium dioxide mixed oxide is its photocatalytic activity, which initiates reactions that can lead to a change in constituents of a sun protection agent. Numerous methods have therefore been developed for lowering the photocatalytic activity of these metal oxides without reducing their UV-screening properties, for example by surrounding them with a shell of silicon dioxide and/or aluminium oxide.

The photoactivity of titanium dioxides can also be reduced by rendering them hydrophobic with organosilanes. A microfine, pyrogenic titanium dioxide that has been established on the market for many years is titanium dioxide T 805 or AEROXIDE $TiO_2$ T 805 (Degussa AG). This product can be prepared by the flame hydrolysis of titanium tetrachloride according to the AEROSIL process and subsequently rendering the product hydrophobic with an organosilane. Pyrogenic titanium-iron mixed oxides that have been rendered hydrophobic are described, for example, in EP 0722992.

However, hydrophobic, pyrogenic titanium dioxides cannot be dispersed in the water phase of a sun protection emulsion but only in the oil phase. However, because the water phase generally accounts for more than 60%, the larger part of a sun protection formulation cannot be used as "carrier" for titanium dioxide. Consequently, the titanium dioxide content of a sun protection emulsion has an upper limit and is generally only from 3 to 5 wt. %, based on the total formulation. This means, that without the addition of further organic UV filters and/or zinc oxides, sun protection agents having a light protection factor >10 are difficult to produce.

Surface-treated hydrophilic, pyrogenic titanium dioxides can be prepared by coating them with silicon dioxide, as described, for example, in DE 10260718 and further publications mentioned therein. However, such materials exhibit a pronounced photoactivity and therefore have only limited suitability for use as UV filters.

Further disadvantages of known hydrophobic and hydrophilic, pyrogenic titanium dioxides are:

insufficient transparency of the sun protection formulations prepared therewith on application to the skin complicated dispersion is necessary a pronounced thickening effect on dispersion in, for example, cosmetic oils or water makes it difficult to prepare dispersions or sun protection agents having a high $TiO_2$ content the sun protection formulations that are prepared feel dull on the skin.

Accordingly, one object in this area is to find a pyrogenically prepared silicon dioxide-titanium dioxide mixed oxide that does not exhibit these disadvantages. A further object to prepare sun protection agents that have improved transparency and sensory properties and that have a high sun protection factor.

DESCRIPTION OF THE INVENTION

The invention provides pyrogenically prepared surface-modified silicon dioxide-titanium dioxide mixed oxides. The surface modification can consist substantially of $SiO_2$, formed from the corresponding starting materials. Alkoxy groups from starting materials (surface-modifying agents) can be present. The surface modification according to the invention may be complete or partial. In addition, the surface-modified pyrogenically prepared silicon dioxide-titanium dioxide mixed oxides according to the invention have a hydrophilic nature.

The invention further provides a process for the preparation of the surface-modified silicon dioxide-titanium dioxide mixed oxides, which process is characterised in that, in a mixer, the pyrogenically prepared silicon dioxide-titanium dioxide mixed oxides are optionally first sprayed with water and then with the surface-modifying agent and are then optionally mixed, and the resulting mixture is tempered. The water that is used can be acidified with an acid, for example hydrochloric acid, to a pH value of from 7 to 1. The water that is used can be rendered alkaline with a lye to a pH value of from 7 to 14. If a plurality of surface-modifying agents are used, these can be applied together, but separately, in succession or in the form of a mixture.

The surface-modifying agent(s) can be dissolved in suitable solvents. When the spraying is complete, mixing can be carried out for from 5 to 30 minutes. The mixture is then subjected to heat treatment at a temperature of from 20 to 400° C. for a period of from 0.1 to 6 hours. The heat treatment can be carried out under protecting gas, such as, for example, nitrogen.

An alternative method for the surface modification of the pyrogenically prepared silicon dioxide-titanium dioxide mixed oxides can be carried out by treating the pyrogenically prepared silicon dioxide-titanium dioxide mixed oxides with the surface-modifying agent in vapour form and then subjecting the mixture to heat treatment.

The heat treatment can be carried out at a temperature of from 50 to 800° C. for a period of from 0.1 to 6 hours. The heat treatment can be carried out under protecting gas, such as, for example, nitrogen. It can also be carried out in a plurality of steps at different temperatures.

The application of the surface-modifying agent(s) can be carried out by means of single-component, two-component or ultrasonic nozzles.

The surface modification can be carried out continuously or batchwise in heatable mixers and driers having spray devices. Suitable devices may be, for example: ploughshare mixers, disk, fluidised bed or fixed bed driers.

When the heat treatment is complete, the oxides according to the invention can be ground. To this end, pinned disk, toothed disk or jet mills can be used.

As pyrogenically prepared silicon dioxide-titanium dioxide mixed oxides there may be used in principle any pyrogenically prepared silicon dioxide-titanium dioxide mixed oxides. There may be used in particular, for example:

a titanium dioxide mixed oxide prepared by flame hydrolysis, that is to say pyrogenically, having a BET surface area of from 10 to 150 m$^2$/g, which comprises from 1 to 30 wt. % silicon dioxide as constituent of the mixed oxide. It is known from DE 4235996, a silicon-titanium dioxide mixed oxide powder prepared by flame hydrolysis, which consists of aggregates of primary particles, characterised in that
the BET surface area is 90±15 m$^2$/g,
the titanium dioxide content is 50±8 wt. %,
the anatase/rutile ratio is from 60:40 to 70:30.
This silicon dioxide-titanium dioxide mixed oxide powder is known from DE 102004024500.2.

a powder consisting of particles having a core of titanium dioxide and a shell of silicon dioxide, which is characterised in that it has a content of silicon dioxide of from 0.5 to 40 wt. %, a BET surface area of from 5 to 300 m$^2$/g and consists of primary particles that have a shell of silicon dioxide and a core of titanium dioxide. This silicon dioxide-titanium dioxide mixed oxide is known from WO 2004/056927.

Accordingly, it is possible to use a powder consisting of particles having a core of titanium dioxide and a shell of silicon dioxide, which powder is characterised in that
it comprises an amount of silicon dioxide of from 0.5 to 40 wt. %,
it has a BET surface area of from 5 to 300 m$^2$/g, and
it consists of primary particles that have a shell of silicon dioxide and a core of titanium dioxide.

The amount of silicon dioxide in the powder according to the invention is from 0.5 to 40 wt. %. With values below 0.5 wt. %, a completely closed silicon dioxide shell is not ensured. At values above 40 wt. %, the UV absorption of the titanium dioxide powders coated with silicon dioxide is too low.

The BET surface area of the powder according to the invention is determined in accordance with DIN 66131.

Primary particles are to be understood as being very small particles which cannot be split up further without breaking chemical bonds. These primary particles can grow together to form aggregates. Aggregates are distinguished by the fact that their surface area is smaller than the sum of the surface areas of the primary particles of which they consist. Furthermore, aggregates are not divided completely into primary particles on dispersion. Powders according to the invention having a low BET surface area may be present wholly or predominantly in the form of non-aggregated primary particles, while powders according to the invention having a high BET surface area have a higher degree of aggregation or are in completely aggregated form. Preferably, the aggregates consist of primary particles which have grown together via their silicon dioxide shells. Powders according to the invention based on such an aggregate structure exhibit particularly low photoactivity while having high absorption. More preferably, the powder according to the invention can have a silicon dioxide content of from 1 to 20 wt. %.

The ratio of the rutile/anatase modifications of the titanium dioxide core of the powder according to the invention can be varied within wide limits. For example, the ratio of the rutile/anatase modifications may be from 1:99 to 99:1, preferably from 10:90 to 90:10. The titanium dioxide modifications exhibit different photoactivity. With the wide limits of the rutile/anatase modifications ratio, together with the silicon dioxide content of the shell, it is possible to select, for example, powders for application in sun protection agents in a targeted manner.

The powder which can be used according to the invention can have an absorption at 320 nm of preferably at least 95%, particularly preferably at least 97%, and at 360 nm preferably of at least 90%, particularly preferably at least 92%. The absorption is determined in each case in an aqueous dispersion of the powder having a solids content of 3 wt. %. The powder which can be used according to the invention can have a photoactivity index of preferably less than 0.5, particularly preferably less than 0.3.

When determining the photoactivity index, the sample to be measured is suspended in 2-propanol and irradiated with UV light for one hour. The concentration of acetone that has formed is then measured. The photoactivity index is the quotient of the acetone concentration determined when using a powder according to the invention, and the acetone concentration determined when using titanium dioxide P25, a pyrogenically prepared titanium dioxide from Degussa. The acetone concentration in mg/kg can be used as a measure of the photocatalytic activity of the sample, because the formation of acetone can be described by a kinetics of zero order according to the equation $dc[Ac]/dt=k$.

The isoelectric point (IEP) of the powder according to the invention can preferably be at a pH value of from 1 to 4, particularly preferably from 2 to 3. Accordingly, stable dispersions can be prepared, for example, in the range from pH 5 to 7 that is of interest for sun protection agents. Titanium dioxide particles without shells result in unstable dispersions in this range, unless further additives are added to the dispersion.

The IEP indicates the pH value at which the zeta potential is zero. In the case of titanium dioxide, the IEP is at a pH of about 5 to 6; in the case of silicon dioxide, it is at about 2 to 4. In dispersions in which the particles carry acidic or basic groups on the surface, the charge can be changed by adjusting the pH value. The greater the difference between the pH value and the IEP, the more stable the dispersion.

The zeta potential is a measure of the surface charge of particles. Zeta potential is to be understood as meaning the potential at the shear plane within the electrochemical double layer particles of the powder according to the invention/electrolyte in a dispersion. The zeta potential is dependent inter alia on the type of particle, for example silicon dioxide, titanium dioxide, titanium dioxide coated with silicon dioxide. Particles of the same material will possess the same sign of the surface charges and will therefore be mutually repellent. If the zeta potential is too small, however, the repelling force is unable to compensate for the van der Waals attraction of the particles, and flocculation and optionally sedimentation of the particles occurs. The zeta potential of the powder according to the invention is determined in an aqueous dispersion.

The powder according to the invention can have a BET surface area of preferably from 40 to 120 m²/g, particularly preferably from 60 to 70 m²/g.

As surface-modifying agents (individual or a plurality) there may be used silicas or organosilanes of the general formula:

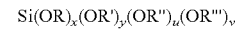

$Si(OR)_x(OR')_y(OR'')_u(OR''')_v$

X=0, 1, 2, 3, 4
y=0, 1, 2, 3, 4
u=0, 1, 2, 3, 4
v=0, 1, 2, 3, 4
x+y+u+v=4
R=alkyl, such as methyl, ethyl, propyl . . .
R'=alkyl, such as methyl, ethyl, propyl . . .
R''=alkyl, such as methyl, ethyl, propyl . . .
R'''=alkyl, such as methyl, ethyl, propyl . . .

It is also possible to use silanes which are formed by the partial hydrolysis and condensation of silanes of type $Si(OR)_x(OR')_y(OR'')_u(OR''')_v$ (as described above), such as, for example, $(CH_3CH_2O)_3SiOSi(CH_3CH_2O)_3$. Such hydrolysis and condensation products can be prepared by oneself or acquired commercially, such as, for example, DYNASIL® 40 (Degussa AG). Preference is given to the use of tetramethoxysilane and tetraethoxysilane.

The invention further provides sun protection agents which comprise from 0.1 to 25 wt. % of a surface-modified, pyrogenically prepared silicon dioxide-titanium dioxide mixed oxide.

The invention further provides sun protection agents which are characterised in that they comprise in the water phase a pyrogenic titanium dioxide surface-treated with silicas and in the oil phase a metal oxide that has been rendered hydrophobic.

The invention relates further to the use of these preparations to protect against UVA and UVB rays.

The sun protection formulations according to the invention of the present invention, as well as comprising one or more oil phases, can preferably additionally comprise one or more water phases and can be in the form of, for example, W/O, O/W, W/O/W or O/W/O emulsions. Such formulations may preferably also be microemulsions, sticks, foams (so-called mousses), solids emulsions (i.e. emulsions stabilised by solids, e.g. Pickering emulsions), sprayable emulsions or hydrodispersions. Furthermore, the preparations may advantageously also be oil-free and/or aqueous-alcoholic solutions.

Also advantageous according to the invention are (macroscopically) two- or multi-phase systems. Within the scope of the present invention, "two- or multi-phase" means that two or more phases are present separately in layers one above the other. It is particularly advantageous within the scope of the present invention for at least one of the macroscopically visible phases to be a (W/O, O/W, micro-) emulsion. When viewed (macroscopically) in this way, the emulsion is perceived to be a phase, although it is, of course, known to the person skilled in the art that emulsions per se are formed by two or more phases which have been homogenised with one another. The "emulsion phase" is stable in the long term, so that no segregation or separation of the phases within the emulsion occurs even over a prolonged period (months, years).

The macroscopically visible phases or layers can advantageously be emulsified in the short term—for example by shaking—to form a homogeneous emulsion which is, however, not stable over the long term but rather separates again over a period of minutes, hours or days into two or more phases in layers one above the other. It is particularly advantageous within the scope of the present invention for at least one of the macroscopically visible phases to be a microemulsion and at least one other of the macroscopically visible phases to be an oil phase.

Sprayable O/W emulsions, in particular O/W microemulsions, are particularly advantageous within the scope of the present invention. The droplet diameters of the emulsions, which are usually "simple", that is to say not multiple, are in the range from about 1 µm to about 50 µm. Without further colouring additives, such "macroemulsions" are milky-white in colour and are opaque. Finer "macroemulsions", whose droplet diameters are in the range from about 0.5 µm to about 1 µm, again without colouring additives, are bluish-white in colour and are opaque. Such "macroemulsions" usually have a high viscosity.

The droplet diameter of microemulsions within the scope of the present invention, on the other hand, is in the range of from approximately 50 to approximately 500 nm. Such microemulsions are bluish-white to translucent and are mostly of low viscosity. The viscosity of many microemulsions of the O/W type is comparable with that of water.

The advantage of microemulsions is that active ingredients can be present in the disperse phase in substantially more finely dispersed form than in the disperse phase of "macroemulsions." A further advantage is that, because of their low viscosity, they are sprayable. If microemulsions are used as cosmetics, corresponding products are distinguished by high cosmetic elegance.

Particularly advantageous according to the invention are O/W microemulsions which are obtainable by means of so-called phase inversion temperature technology and comprise at least one emulsifier (emulsifier A) selected from the group of emulsifiers having the following properties:
their lipophily is dependent on the temperature, so that by increasing the temperature the lipophily increases and by lowering the temperature the lipophily of the emulsifier decreases.

Advantageous emulsifiers A are, for example, polyethoxylated fatty acids (PEG-100 stearate, PEG-20 stearate, PEG-150 laurath, PEG-8 distearate and the like) and/or or polyethoxylated fatty alcohols (cetearath-12, cetearath-20, isoceteth-20, beheneth-20, laurath-9, etc.) and/or alkyl polyglycosides (cetearyl glycoside, stearyl glycoside, palmityl glycoside, etc.).

Provided the phase inversion is initiated substantially by varying the temperature, O/W emulsions, in particular O/W microemulsions, are obtainable, the size of the oil droplets being determined substantially by the concentration of the emulsifier(s) used, such that a higher emulsifier concentration produces smaller droplets and a lower emulsifier concentration results in larger droplets. The droplet sizes are generally from 20 to 500 nm.

It may be advantageous within the scope of the present invention to use further W/O and/or O/W emulsifiers that do not fall within the definition of emulsifier A, for example in order to increase the hygrostability of the preparations according to the present invention. There may be used here, for example, alkyl methicone copolyols and/or alkyl dimethicone copolyols (in particular cetyl dimethicone copolyol, lauryl methicone copolyol), W/O emulsifiers (for example sorbitan stearate, glyceryl stearate, glycerol stearate, sorbitan oleate, lecithin, glyceryl isostearate, polyglyceryl-3-oleate, polyglyceryl-3-diisostearate, PEG-7 hydrogenated castor oil, polyglyceryl-4-distearate, acrylate/C10-30-alkyl acrylate crosspolymer, sorbitan isostearate, poloxamer 101, polyglyceryl-2-dipolyhydroxy stearate, polyglyceryl-3-diisostearate, polyglyceryl-4-dipolyhydroxy stearate, PEG-30 dipolyhydroxystearate, diisostearoylpolyglyceryl-3-diisostearate, glycol distearate, polyglyceryl-3-dipolyhydroxystearate) and/or fatty acid esters of sulfuric acid or phosphoric acid (cetyl phosphate, trilaureth-4 phosphate, trioleth-8 phosphate, stearyl phosphate, cetearyl sulfate, etc.).

Further advantageous sprayable O/W emulsions within the scope of the present invention are low-viscosity cosmetic or dermatological hydrodispersions comprising at least one oil phase and at least one water phase, wherein the preparation is stabilised by at least one gel former and does not necessarily have to comprise emulsifiers but may comprise one or more emulsifiers.

Advantageous gel formers for such preparations are, for example, copolymers of C10-30-alkyl acrylates and one or more monomers of acrylic acid, methacrylic acid or esters thereof. The INCI name for such compounds is "Acrylates/C10-30Alkyl Acrylate Crosspolymer". The Pemulen® types TR1, TR2 and TRZ from Goodrich (Noveon) are particularly advantageous. Carbopols are also advantageous gel formers for such preparations. Carbopols are polymers of acrylic acid, in particular also acrylate-alkyl acrylate copolymers. Advantageous carbopols are, for example, the types 907, 910, 934, 940, 941, 951, 954, 980, 981, 1342, 1382, 2984 and 5984, as well as the ETD types 2020, 2050 and carbopol Ultrez 10. Further advantageous gel formers for such preparations are xanthan gum, cellulose derivatives and locust bean flour. Possible (optional) emulsifiers which can be used are ethoxylated fatty alcohols or ethoxylated fatty acids (in particular PEG-100 stearate, ceteareth-20) and/or other non-ionic surface-active substances.

Also advantageously, the very low-viscosity to sprayable emulsions may also be W/O or water-in-silicone oil (W/S) emulsions. Particularly advantageous are W/O or W/S emulsions which comprise at least one silicone emulsifier (W/S) having a HLB value ≦8 and/or at least one W/O emulsifier having a HLB value <7 and at least one O/W emulsifier having a HLB value >10. Such preparations further comprise at least 20 wt. % lipids, it being possible for the lipid phase advantageously to comprise also silicone oils or even to consist wholly of such oils. The silicone emulsifier(s) can advantageously be selected from the group of the alkyl methicone copolyols and/or alkyl dimethicone copolyols (e.g. dimethicone copolyols marketed by Goldschmidt AG under the trade marks ABIL® B 8842, ABIL® B 8843, ABIL® B 8847, ABIL® B 8851, ABIL® B 8852, ABIL® B 8863, ABIL® B 8873 and ABIL® B 88183, cetyl dimethicone copolyol [Goldschmidt AG/ABIL® EM 90], cyclomethicone dimethicone copolyol [Goldschmidt AG/ABIL® EM 97], lauryl methicone copolyol [Dow Corning Ltd. I Dow Corning 5200 Formulation Aid], octyl dimethicone ethoxy glucoside [Wacker].

The W/O emulsifier(s) having a HLB value <7 can advantageously be selected from the following group: sorbitan stearate, sorbitan oleate, lecithin, glyceryl lanolate, lanolin, hydrogenated castor oil, glyceryl isostearate, polyglyceryl-3-oleate, pentaerythrityl isostearate, methyl glucose dioleate, methyl glucose dioleate in admixture with hydroxy stearate and beeswax, PEG-7 hydrogenated castor oil, polyglyceryl-4-isostearate, hexyl laurate, acrylate/$C_{10-30}$-alkyl acrylate crosspolymer, sorbitan isostearate, polyglyceryl-2-dipolyhydroxystearate, polyglyceryl-3-diisostearate, PEG-30 dipolyhydroxystearate, diisostearoylpolyglyceryl-3-diisostearate, polyglyceryl-3-dipolyhydroxystearate, polyglyceryl-4-dipolyhydroxystearate, polyglyceryl-3-dioleate.

The O/W emulsifier(s) having a HLB value >10 can advantageously be selected from the following group: glyceryl stearate in admixture with ceteareth-20, ceteareth-25, ceteareth-6 in admixture with stearyl alcohol, cetylstearyl alcohol in admixture with PEG-40 castor oil and sodium cetylstearyl sulfate, triceteareth-4 phosphate, glyceryl stearate, sodium cetylstearyl sulfate, lecithin trilaureth-4 phosphate, laureth-4 phosphate, stearic acid, propylene glycol stearate SE, PEG-9 stearate, PEG-20 stearate, PEG-30 stearate, PEG-40 stearate, PEG-100 stearate, ceteth-2, ceteth-20, polysorbate-20, polysorbate-60, polysorbate-65, polysorbate-100, glyceryl stearate in admixture with PEG-100 stearate, ceteareth-3, isostearyl glyceryl ether, cetylstearyl alcohol in admixture with sodium cetylstearyl sulfate, PEG-40 stearate, glycol distearate, polyglyceryl-2-PEG-4-stearate, ceteareth-12, ceteareth-20, ceteareth-30, methyl glucose sesquistearate, steareth-10, PEG-20 stearate, steareth-21, steareth-20, isosteareth-20, PEG-45/dodecyl glycol copolymer, glyceryl stearate SE, ceteth-20, PEG-20 methyl glucose sesquistearate, glyceryl stearate citrate, cetyl phosphate, cetearyl sulfate, sorbitan sesquioleate, triceteareth-4-phosphate, trilaureth-4-phosphate, polyglyceryl methyl glucose distearate, potassium cetyl phosphate, isosteareth-10, polyglyceryl-2-sesquiisostearate, ceteth-10, isoceteth-20, glyceryl stearate in admixture with ceteareth-20, ceteareth-12, cetylstearyl alcohol and cetyl palmitate, PEG-30 stearate, PEG-40 stearate, PEG-100 stearate.

Also advantageous are aqueous-alcoholic solutions. They can comprise from 0 wt. % to 90 wt. % ethanol. Within the scope of the present invention, aqueous-alcoholic solutions can advantageously also comprise solubilisers, for example PEG-40 or PEG-60 hydrogenated castor oil.

The preparations according to the present invention can advantageously also be used as cosmetic or dermatological impregnating solutions, with which water-insoluble substrates in particular—such as, for example, woven or non-woven cloths—are moistened. Such impregnating solutions are preferably of low viscosity, in particular sprayable (such as, for example, PIT emulsions, hydrodispersions, W/O emulsions, oils, aqueous solutions, etc.) and preferably have a viscosity of less than 2000 mPa s, in particular less than 1500 mPa s (measuring device: Haake Viskotester VT 02 at 25° C.). Using such impregnating solutions it is possible to obtain, for example, cosmetic sun protection cloths, care cloths and the like which represent a combination of a soft, water-insoluble material with the low-viscosity cosmetic and dermatological impregnating solution.

The preparations according to the present invention may advantageously also be in the form of anhydrous oils or oil gels or pastes. Advantageous oils are, for example, synthetic, semi-synthetic or natural oils, such as, for example, rape oil, rice oil, avocado oil, olive oil, mineral oil, cocoglycerides, butylene glycol dicaprylate/dicaprate, $C_{12}$-$C_{15}$-alkyl benzoate, dicaprylyl carbonate, octyldodecanol and the like. As oil-gel formers there may be used a very wide variety of waxes having a melting point >25° C. Also advantageous are gel formers from the group of the Aerosils, the alkylgalactomannans (e.g. N-Hance AG 200 and N-Hance AG 50 from Hercules) and polyethylene derivatives.

Within the scope of the present invention, self-foaming, foam-like, after-foaming or foamable cosmetic and dermatological preparations are also particularly advantageous. "Self-foaming", "foam-like", "after-foaming" and "foamable" are to be understood as meaning preparations from which foams can in principle be produced—either during the preparation process, during use by the consumer or in another manner—by the introduction of one or more gases. In such foams, the gas bubbles are distributed (in any desired manner) in one (or more) liquid phase(s), it not being necessary for the (foamed) preparations to have, macroscopically, the appearance of a foam. (Foamed) cosmetic or dermatological preparations according to the invention (also referred to hereinbelow as foams for the sake of simplicity) can, for example, represent, macroscopically visibly, dispersed systems of gases dispersed in liquids. However, it may also be possible to see the foam nature, for example, only under a (light) microscope. Moreover, foams according to the invention—in particular when the gas bubbles are too small to be detected under a light microscope—are also recognisable by the pronounced increase in volume of the system.

It was particularly surprising, that the use of the alpha olefin/maleic anhydride copolymers according to the invention assists the introduction of gases and that a stabilising and markedly foam-increasing effect can be achieved over a prolonged storage period even at higher temperatures (e.g. 40° C.). It was particularly surprising that it is possible to dispense with the use of special surfactants. The introduction of gases is, surprisingly, increased extraordinarily compared with the prior art. For example, a foam enhancement with a gas volume increased by up to 100% can be achieved without the use of foaming agents, such as surfactants, which are conventional according to the prior art. As a result it is possible stably to generate recipes having a high gas volume (air and/or other gases, such as oxygen, carbon dioxide, nitrogen, helium, argon, etc.) over a long storage period at high temperatures. The invention therefore relates further to the use of one or more alpha olefin/maleic anhydride copolymers for enhancing the foaming of self-foaming, foam-like, after-foaming or foamable cosmetic and dermatological preparations.

Within the scope of the present invention, "foam enhancement" is to be understood as meaning that the introduction of gases into the foams according to the invention is increased extraordinarily compared with the introduction into otherwise identical preparations that do not comprise alpha olefin/maleic anhydride copolymers according to the invention. The foams according to the invention are accordingly able to take up a markedly higher gas volume than preparations that do not comprise alpha olefin/maleic anhydride copolymers according to the invention. "Foam enhancement" additionally means that the stability of the foamed preparations (the "foam stability") is markedly improved compared with otherwise identical preparations that do not comprise alpha olefin/maleic anhydride copolymers according to the invention, that is to say the breaking up of the foams is retarded in terms of time by the use according to the invention. Within the scope of the present invention, such preparations advantageously comprise an emulsifier system consisting of A) at least one emulsifier A selected from the group of the wholly neutralised, partially neutralised or unneutralised, branched and/or unbranched, saturated and/or unsaturated fatty acids having a chain length of from 10 to 40 carbon atoms, B) at least one emulsifier B selected from the group of the polyethoxylated fatty acid esters having a chain length of from 10 to 40 carbon atoms and having a degree of ethoxylation of from 5 to 100, and C) at least one coemulsifier C selected from the group of the saturated and/or unsaturated, branched and/or unbranched fatty alcohols having a chain length of from 10 to 40 carbon atoms.

The emulsifier(s) A is/are preferably selected from the group of the fatty acids which have been completely or partially neutralised with conventional alkalis (such as, for example, sodium and/or potassium hydroxide, sodium and/or potassium carbonate and mono- and/or tri-ethanolamin). Examples of particularly advantageous fatty acids are stearic acid and stearates, isostearic acid and isostearates, palmitic acid and palmitates as well as myristic acid and myristates. The emulsifier(s) B is/are preferably selected from the following group: PEG-9 stearate, PEG-8 distearate, PEG-20 stearate, PEG-8 stearate, PEG-8 oleate, PEG-25 glyceryl trioleate, PEG-40 sorbitan lanolate, PEG-15 glyceryl ricinoleate, PEG-20 glyceryl stearate, PEG-20 glyceryl isostearate, PEG-20 glyceryl oleate, PEG-20 stearate, PEG-20 methyl glucose sesquistearate, PEG-30 glyceryl isostearate, PEG-20 glyceryl laurate, PEG-30 stearate, PEG-30 glyceryl stearate, PEG-40 stearate, PEG-30 glyceryl laurate, PEG-50 stearate, PEG-100 stearate, PEG-150 laurate. Polyethoxylated stearic acid esters, for example, are particularly advantageous.

The coemulsifier(s) C is/are preferably selected according to the invention from the following group: behenyl alcohol ($C_{22}H_{45}OH$), ceteary1 alcohol [a mixture of cetyl alcohol ($C_{16}H_{33}OH$) and stearyl alcohol ($C_{18}H_{37}OH$)], lanolin alcohols (wool wax alcohols which represent the unsaponifiable alcohol fraction of wool wax that is obtained after the saponification of wool wax). Particular preference is given to cetyl alcohol and cetylstearyl alcohol.

It is advantageous according to the invention to choose the weight ratios of emulsifier A to emulsifier B to coemulsifier C (A:B:C) as a:b:c, wherein a, b and c, independently of one another, may represent rational numbers from 1 to 5, preferably from 1 to 3. Particular preference is given to a weight ratio of approximately 1:1:1.

It is advantageous within the scope of the present invention to choose the total amount of the emulsifiers A and B and of the coemulsifier C from the range from 2 to 20 wt. %, advantageously from 5 to 15 wt. %, especially from 7 to 13 wt. %, in each case based on the total weight of the formulation.

Particularly advantageous within the scope of the present invention are also cosmetic or dermatological preparations which are stabilised only by very finely divided solids particles. Such "emulsifier-free" emulsions are also referred to as Pickering emulsions. In Pickering emulsions, the solid substance becomes concentrated in the form of a layer at the oil/water interface, which prevents the disperse phases from flowing together. The surface properties of the solids particles are of substantial importance here, which solids particles should exhibit both hydrophilic and lipophilic properties.

Advantageously, the stabilising solids particles may also be treated in a water-repellent manner on the surface ("coated"), whereby an amphiphilic nature of these solids particles should be formed or retained. The surface treatment can consist in providing the solids particles with a thin hydrophobic or hydrophilic layer by processes known per se.

The mean particle diameter of the microfine solids particles used as stabiliser is preferably chosen to be less than 100 μm, particularly advantageously less than 50 μm. The form (plates, rods, spheres, etc.) or modification of the solids particles used is substantially unimportant.

The microfine solids particles are preferably selected from the group of the amphiphilic metal oxide pigments. The following are particularly advantageous:

titanium dioxides (coated and uncoated): e.g. Eusolex T-2000 from Merck, titanium dioxide MT 100 Z from Tayca Corporation zinc oxides, e.g. Z-Cote and Z-Cote HP1 from BASF AG, MZ-300, MZ-500 and MZ-505M from Tayca Corporation iron oxides.

It is further advantageous if the microfine solids particles are selected from the following group: boron nitrides, starch derivatives (tapioca starch, sodium corn starch, octynyl succinate, etc.), talcum, latex particles.

It is advantageous according to the invention if the solids-stabilised emulsions contain markedly less than 0.5 wt. % of one or more emulsifiers or are even completely free of emulsifiers.

Also advantageous within the scope of the invention are preparations in the form of sticks. From the technical point of view, most stick formulations are anhydrous fat mixtures of solid or semi-solid waxes and liquid oils, highly purified paraffin oils and paraffin waxes constituting the base substance of the stick. Conventional base substances for preparations in stick form are, for example, liquid oils (such as, for example, paraffin oils, castor oil, isopropyl myristate, $C_{12-15}$-alkyl benzoate), semi-solid constituents (e.g. Vaseline, lanolin), solid constituents (e.g. beeswax, ceresine and microcrystalline waxes or ozokerite) and/or high melting waxes (e.g. carnauba wax, candelilla wax). Water-containing preparations in stick form are also known per se, which preparations can also be in the form of W/O emulsions.

The cosmetic or dermatological light protection formulations according to the invention can be composed in the conventional manner and be used for cosmetic and dermatological light protection, also for the treatment, care and cleansing of the skin and/or the hair and as a make-up product in decorative cosmetics. According to their structure, cosmetic or topical dermatological compositions within the scope of the present invention can be used, for example, as a skin protection cream, cleansing milk, day or night cream, etc. It is optionally possible and advantageous to use the compositions according to the invention as the basis for pharmaceutical formulations. For application, the cosmetic and dermatological preparations are applied to the skin and/or the hair in a sufficient amount in the manner conventional for cosmetics.

The cosmetic and dermatological preparations according to the invention can comprise cosmetic auxiliary substances, as are conventionally employed in such preparations, for example preservatives, preservation aids, complexing agents, bactericides, perfumes, substances for preventing or increasing foaming, colourings, pigments that have a colouring effect, thickeners, moisturising substances and/or humectants, fillers that improve the feeling on the skin, fats, oils, waxes or other conventional constituents of a cosmetic or dermatological formulation, such as alcohols, polyols, polymers, foam stabilisers, electrolytes, organic solvents or silicone derivatives.

Advantageous preservatives within the scope of the present invention are, for example, formaldehyde-cleaving agents (such as, for example, DMDM hydantoin, which is obtainable, for example, from Lonza under the trade name Glydant™), iodopropyl butylcarbamates (e.g. those obtainable under the trade names Glycacil-L, Glycacil-S from Lonza and/or Dekaben LMB from Jan Dekker), parabens (i.e. p-hydroxybenzoic acid alkyl esters, such as methyl-, ethyl-, propyl- and/or butyl-paraben), phenoxyethanol, ethanol, benzoic acid and the like. According to the invention, the preservative system conventionally also comprises, advantageously, preservation aids, such as, for example, octoxyglycerol, glycine soya, etc. Advantageous complexing agents within the scope of the present invention are, for example, EDTA, [S,S]-ethylenediamine disuccinate (EDDS), which is obtainable, for example, under the trade name Octaquest from Octel, pentasodium ethylenediaminetetramethylenephosphonate, which is obtainable, for example, under the trade name Dequest 2046 from Monsanto, and/or iminodisuccinic acid, which is obtainable inter alia from Bayer AG under the trade names Iminodisuccinat VP OC 370 (approx. 30% solution) and Baypure CX 100 solid.

Particularly advantageous preparations are further obtained by using antioxidants as additives or active ingredients. According to the invention, the preparations advantageously comprise one or more antioxidants. Advantageous but nevertheless optional antioxidants that may be used are all antioxidants that are suitable or conventional for cosmetic and/or dermatological applications.

It is particularly advantageous within the scope of the present invention to use water-soluble antioxidants, such as, for example, vitamins, e.g. ascorbic acid and derivatives thereof. Preferred antioxidants are further vitamin E and its derivatives as well as vitamin A and its derivatives. The amount of antioxidants (one or more compounds) in the preparations is preferably from 0.001 to 30 wt. %, particularly preferably from 0.05 to 20 wt. %, especially from 0.1 to 10 wt. %, based on the total weight of the preparation.

If vitamin E and/or its derivatives constitute(s) the antioxidant(s), it is advantageous to choose the respective concentrations thereof from the range from 0.001 to 10 wt. %, based on the total weight of the formulation.

If vitamin A or vitamin A derivatives, or carotenes or derivatives thereof, constitute(s) the antioxidant(s), it is advantageous to choose the respective concentrations thereof from the range from 0.001 to 10 wt. %, based on the total weight of the formulation.

It is particularly advantageous if the cosmetic preparations according to the present invention comprise cosmetic or dermatological active ingredients, preferred active ingredients being antioxidants, which can protect the skin from oxidative damage.

Further advantageous active ingredients within the scope of the present invention are natural active ingredients and/or derivatives thereof, such as, for example, alpha-liponic acid, phytoene, D-biotin, coenzyme Q10, alpha-glucosylrutin, carnitine, carnosine, natural and/or synthetic isoflavonoids, creatine, taurine and/or beta-alanine, as well as 8-hexadecene-1,16-dicarboxylic acid (dioic acid, CAS number 20701-68-2; preliminary INCI name octadecenedioic acid).

Recipes according to the invention that comprise, for example, known anti-wrinkle active ingredients such as flavone glycosides (in particular alpha-glycosylrutin), coenzyme Q10, vitamin E and/or derivatives and the like, are advantageously suitable in particular for the prophylaxis and treatment of cosmetic or dermatological skin changes such as occur, for example, in the case of skin ageing (such as, for example, dryness, roughness and formation of dryness lines, itching, reduced re-greasing (e.g. after washing), visible dilatation of capillaries (telangiectasis, cuperosis), slackness and development of wrinkles and lines, local hyperpigmentation, hypopigmentation and lack of pigmentation (e.g. age marks), increased susceptibility to mechanical stress (e.g. chapping) and the like). They are also advantageously suitable against the symptoms of dry or rough skin.

The water phase of the preparations according to the present invention can advantageously comprise conventional cosmetic auxiliary substances, such as, for example, alcohols, in particular those having a low C number, preferably ethanol and/or isopropanol, diols or polyols having a low C number, as well as ethers thereof, preferably propylene glycol, glycerol, butylene glycol, ethylene glycol, ethylene glycol monomethyl or monobutyl ether, propylene glycol monomethyl, monoethyl or monobutyl ether, diethylene glycol monomethyl or monoethyl ether and analogous products, polymers, foam stabilisers, electrolytes and, in particular, one or more thickeners which can advantageously be selected from the group silicon dioxide, aluminium silicates, polysaccharides and derivatives thereof, e.g. hyaluronic acid, xanthan gum, hydroxypropylmethyl-cellulose, particularly advantageously from the group of the polyacrylates, preferably a polyacrylate from the group of the so-called carbopols [from Bf. Goodrich], for example carbopols of types 980, 981, 1382, 2984, 5984, ETD 2020, ETD 2050, Ultrez 10, in each case individually or in combination.

The preparations according to the present invention can advantageously also comprise self-tanning substances, such as, for example, dihydroxyacetone and/or melanine derivatives, in concentrations of from 1 wt. % to 8 wt. %, based on the total weight of the preparation.

Also advantageously, the preparations according to the present invention can also comprise repellents for protection against mosquitoes, ticks and spiders and the like. Advantageous repellents are, for example, N,N-diethyl-3-methylbenzamide (trade name: Metadelphene, "DEET"), dimethyl phthalate (trade name: Palatinol M, DMP) and, in particular, 3-(N-n-butyl-N-acetyl-amino)-propionic acid ethyl ester (obtainable under the trade name Insekt Repellent™ 3535 from Merck). The repellents can be used both individually and in combination.

Moisturisers are substances or mixtures of substances that confer on cosmetic or dermatological preparations the property that, after application to or distribution on the skin surface, they reduce the transepidermal water loss (TEWL) and/or influence in a positive manner the hydration of the epidermis. Advantageous moisturisers within the scope of the present invention are, for example, glycerol, lactic acid and/or lactates, in particular sodium lactate, butylene glycol, propylene glycol, biosaccharide gum-1, glycine soya, ethylhexyloxyglycerol, pyrrolidonecarboxylic acid and urea. It is also particularly advantageous to use polymeric moisturisers from the group of the polysaccharides that are water-soluble and/or swellable in water and/or can be made into a gel with the aid of water. Examples of particularly advantageous moisturisers are hyaluronic acid, chitosan and/or a fucose-rich polysaccharide which has been deposited in Chemical Abstracts under registration number 178463-23-5 and is obtainable, for example, under the name Fucogel™ 1000 from SOLABIA S.A. Moisturisers can advantageously also be used as anti-wrinkle active ingredients for the prophylaxis and treatment of cosmetic or dermatological skin changes such as occur, for example, in the case of skin ageing.

Although not absolutely necessary, the cosmetic or dermatological preparations according to the invention can advantageously also comprise fillers which, for example, further improve the sensory and cosmetic properties of the formulations and, for example, bring about or enhance a velvety or silky feel on the skin. Advantageous fillers within the scope of the present invention are starches and starch derivatives (such as, for example, tapioca starch, distarch phosphate, aluminium or sodium starch octenylsuccinate and the like), pigments which have predominantly neither a UV-filtering nor colouring action (such as, for example, boron nitride, etc.), and/or Aerosils®.

The oil phase of the formulations according to the invention is advantageously selected from the group of the polar oils, for example from the group of the lecithins and of the fatty acid triglycerides, specifically the triglycerol esters of saturated and/or unsaturated, branched and/or unbranched alkanecarboxylic acids having a chain length of from 8 to 24 carbon atoms, in particular from 12 to 18 carbon atoms. The fatty acid triglycerides can advantageously be selected, for example, from the group of the synthetic, semi-synthetic and natural oils, such as, for example, cocoglyceride, olive oil, sunflower oil, soya oil, groundnut oil, rape oil, almond oil, palm oil, coconut oil, castor oil, wheatgerm oil, grapeseed oil, thistle oil, evening primrose oil, macadamia nut oil and the like.

Also advantageous according to the invention are, for example, natural waxes of animal and vegetable origin, such as, for example, beeswax and other insect waxes as well as berry wax, shea butter and/or lanolin (wool wax).

Further advantageous polar oil components within the scope of the present invention can further be selected from the group of the esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, as well as from the group of the esters of aromatic carboxylic acids and saturated and/or unsaturated, branched and/or unbranched alcohols having a chain length of from 3 to 30 carbon atoms. Such ester oils can, then, advantageously be selected from the group octyl palmitate, octyl cocoate, octyl isostearate, octyl dodecylmyristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, as well as synthetic, semi-synthetic and natural mixtures of such esters, such as, for example, jojoba oil.

The oil phase can advantageously further be selected from the group of the dialkyl ethers and dialkyl carbonates; of advantage are, for example, dicaprylyl ethers (Cetiol OE) and/or dicaprylyl carbonate, for example that obtainable under the trade name Cetiol CC from Cognis. It is further preferred to select the oil component(s) from the group isoeicosan, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is particularly advantageous if the oil phase of the formulations according to the invention has a content of $C_{12-15}$-alkyl benzoate or consists wholly thereof. Advantageous oil components are also, for example, butyloctyl salicylate (for example that obtainable under the trade name Hallbrite BHB from CP Hall), hexadecyl benzoate and butyloctyl benzoate and mixtures thereof (Hallstar AB) and/or diethylhexyl naphthalate (Hallbrite TQ or Corapan TQ from H&R). Any desired blends of such oil and wax components can also advantageously be used within the scope of the present invention.

The oil phase may further likewise advantageously comprise non-polar oils, for example those which are selected from the group of the branched and unbranched hydrocarbons and waxes, in particular mineral oil, Vaseline (petrolatum), paraffin oil, squalane and squalene, polyolefins, hydrogenated polyisobutenes and isohexadecane. Among the polyolefins, polydecenes are the preferred substances.

The oil phase may advantageously further have a content of cyclic or linear silicone oils or consist wholly of such oils, it being preferred, however, to use, in addition to the silicone oil(s), an additional content of other oil phase components. Silicone oils are high molecular weight synthetic polymeric compounds in which silicon atoms are linked via oxygen atoms in the manner of a chain and/or network and the residual valences of the silicon are saturated by hydrocarbon radicals (mostly methyl, more rarely ethyl, propyl, phenyl groups and the like). Systematically, the silicone oils are referred to as polyorganosiloxanes. The methyl-substituted polyorganosiloxanes, which represent the most important compounds of this group in terms of amount and are distinguished by the following structural formula

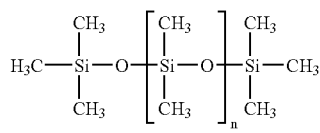

are also referred to as polydimethylsiloxane or dimethicone (INCI). Dimethicone is available in various chain lengths and with various molecular weights.

Particularly advantageous polyorganosiloxanes within the scope of the present invention are, for example, dimethylpolysiloxanes [poly(dimethylsiloxane)], which are obtainable, for example, under the trade names Abil 10 to 10,000 from Th. Goldschmidt. Also advantageous are phenylmethylpolysiloxanes (INCI: phenyl dimethicone, phenyl trimethicone), cyclic silicones (octamethylcyclotetrasiloxane or decamethylcyclopentasiloxane), which according to INCI are also referred to as cyclomethicones, amino-modified silicones (INCI: amodimethicones) and silicone waxes, e.g. polysiloxane-polyalkylene copolymers (INCI: stearyl dimethicone and cetyl dimethicone) and dialkoxydimethylpolysiloxanes (stearoxy dimethicone and behenoxy stearyl dimethicone), which are obtainable as various Abil wax types from Th. Goldschmidt. However, other silicone oils can also advantageously be used within the scope of the present invention, for example cetyl dimethicone, hexamethylcyclotrisiloxane, polydimethylsiloxane, poly(methylphenylsiloxane).

The preparations according to the present invention can further advantageously comprise one or more substances from the following group of the siloxane elastomers, for example in order to increase the hygrostability and/or the light protection factor of the products:

a) siloxane elastomers which contain the units $R_2SiO$ and $RSiO_{1.5}$ and/or $R_3SiO_{0.5}$ and/or $SiO_2$, the individual radicals R, each independently of the others, representing hydrogen, $C_{1-24}$-alkyl (such as, for example, methyl, ethyl, propyl) or aryl (such as, for example, phenyl or tolyl), alkenyl (such as, for example, vinyl) and the weight ratio of the units R2SiO to $RSiO_{1.5}$ being selected from the range from 1:1 to 30:1;

b) siloxane elastomers that are insoluble and swellable in silicone oil, which are obtainable by the addition reaction of an organopolysiloxane (1) containing silicon-bonded hydrogen with an organopolysiloxane (2) containing unsaturated aliphatic groups, the relative amounts used being so chosen that the amount of hydrogen in the organopolysiloxane (1) or in the unsaturated aliphatic groups of the organopolysiloxane (2)

is in the range from 1 to 20 mol. % when the organopolysiloxane is not cyclic and is in the range from 1 to 50 mol. % when the organopolysiloxane is cyclic.

Within the scope of the present invention, the siloxane elastomer(s) is/are advantageously in the form of spherical powders or in the form of gels. Siloxane elastomers in the form of spherical powders that are advantageous according to the invention are those having the INCI name dimethicone/vinyl dimethicone crosspolymer, for example that which is obtainable from DOW CORNING under the trade name DOW CORNING 9506 Powder. It is particularly preferred for the siloxane elastomer to be used in combination with oils from hydrocarbons of animal and/or vegetable origin, synthetic oils, synthetic esters, synthetic ethers or mixtures thereof.

It is very particularly preferred for the siloxane elastomer to be used in combination with unbranched silicone oils that are liquid or pasty at room temperature or cyclic silicone oils or mixtures thereof. Particularly advantageous are organopolysiloxane elastomers having the INCI name dimethicone/polysilicone-11, very particularly the Gransil types GCM, GCM-5, DMG-6, CSE Gel, PM-Gel, LTX, ININ Gel, AM-18 Gel and/or DMCM-5 obtainable from Grant Industries Inc.

It is especially preferred for the siloxane elastomer to be used in the form of a gel of siloxane elastomer and a lipid phase, the content of the siloxane elastomer in the gel being from 1 to 80 wt. %, preferably from 10 to 60 wt. %, in each case based on the total weight of the gel. It is advantageous within the scope of the present invention to choose the total amount of siloxane elastomers (active content) from the range from 0.01 to 10 wt. %, advantageously from 0.1 to 5 wt. %, in each case based on the total weight of the formulation. The cosmetic and dermatological preparations according to the invention can comprise colourings and/or colouring pigments, in particular when they are in the form of decorative cosmetics. The colourings and colouring pigments can be chosen from the corresponding positive list of the decree on cosmetics or the EC list of cosmetic colouring agents. In most cases, they are identical with the colourings permissible for foodstuffs. Advantageous colouring pigments are, for example, titanium dioxide, mica, iron oxides (e.g. Fe2O3, Fe3O4, FeO(OH)) and/or tin oxide. Advantageous colourings are, for example, carmine, Prussian blue, chromic oxide green, ultramarine blue and/or manganese violet. It is particularly advantageous to choose the colourings and/or colouring pigments from the Rowe Colour Index, 3rd edition, Society of Dyers and Colourists, Bradford, England, 1971.

If the formulations according to the invention are in the form of products which are applied to the face, it is advantageous to choose as colourings one or more substances from the following group: 2,4-dihydroxyazobenzene, 1-(2'-chloro-4'-nitro-1'-phenylazo)-2-hydroxynaphthalene, ceres red, 2-(sulfo-1-naphthylazo)-1-naphthol-4-sulfo acid, calcium salt of 2-hydroxy-1,2'-azonaphthalene-1'-sulfo acid, calcium and barium salts of 1-(2-sulfo-4-methyl-1-phenylazo)-2-naphthyl-carboxylic acid, calcium salt of 1-(2-sulfo-1-naphthylazo)-2-hydroxynaphthalene-3-carboxylic acid, aluminium salt of 1-(4-sulfo-1-phenylazo)-2-naphthol-6-sulfo acid, aluminium salt of 1-(4-sulfo-1-naphthylazo)-2-naphthol-3,6-disulfo acid, 1-(4-sulfo-1-naphthylazo)-2-naphthol-6,8-disulfo acid, aluminium salt of 4-(4-sulfo-1-phenylazo)-1-(4-sulfophenyl)-5-hydroxy-pyrazolone-3-carboxylic acid, aluminium and zirconium salts of 4,5-dibromofluorescein, aluminium and zirconium salts of 2,4,5,7-tetrabromofluorescein, 3',4',5',6',-tetrachloro-2,4,5,7-tetrabromofluorescein and its aluminium salt, aluminium salt of 2,4,5,7-tetraiodofluorescein, aluminium salt of quinophthalone-disulfo acid, aluminium salt of indigo-disulfo acid, red and black iron oxide (CIN: 77 491 (red) and 77 499 (black)), iron oxide hydrate (CIN: 77 492), manganeseammonium diphosphate and titanium dioxide.

Also advantageous are oil-soluble natural colourings, such as, for example, paprika extracts, beta-carotene or cochineal.

Also advantageous within the scope of the present invention are formulations comprising pearl lustre pigments. Preference is given in particular to the types of pearl lustre pigments mentioned hereinbelow:

1. natural pearl lustre pigments, such as, for example,
    "fish silver" (guanine/hypoxanthine mixed crystals from fish scales) and
    "mother of pearl" (ground mussel shells)
2. monocrystalline pearl lustre pigments, such as, for example, bismuth oxychloride (BiOCl)
3. layer-substrate pigments: e.g. mica/metal oxide Pearl lustre pigments are based, for example, on pulverulent pigments or castor oil dispersions of bismuth oxychloride and/or titanium dioxide as well as bismuth oxychloride and/or titanium dioxide on mica. The lustre pigment listed under CIN 77163, for example, is particularly advantageous.

Also advantageous are, for example, the following types of pearl lustre pigments based on mica/metal oxide:

| Group | Coating/layer thickness | Colour |
|---|---|---|
| Silver-white pearl lustre pigments | TiO$_2$: 40–60 nm | silver |

| Group | Coating/layer thickness | Colour |
|---|---|---|
| Interference pigments | TiO$_2$: 60–80 nm | yellow |
| | TiO$_2$: 80–100 nm | red |
| | TiO$_2$: 120–160 nm | green |
| Colour lustre pigments | Fe$_2$O$_3$ | bronze |
| | Fe$_2$O$_3$ | copper |
| | Fe$_2$O$_3$ | red |
| | Fe$_2$O$_3$ | red-violet |
| | Fe$_2$O$_3$ | reddish-green |
| | Fe$_2$O$_3$ | black |
| Combination pigments | TiO$_2$/Fe$_2$O$_3$ | gold tones |
| | TiO$_2$/Cr$_2$O$_3$ | green |
| | TiO$_2$/Prussian blue | deep blue |
| | TiO$_2$/carmine | red |

Particular preference is given, for example, to the pearl lustre pigments obtainable from Merck under the trade names Timiron, Colorona or Dichrona.

The list of mentioned pearl lustre pigments is, of course, not intended to be limiting. Pearl lustre pigments that are advantageous within the scope of the present invention are obtainable by many methods known per se. For example, substrates other than mica may also be coated with further metal oxides, such as, for example, silica and the like. SiO$_2$ particles coated, for example, with TiO$_2$ and Fe$_2$O$_3$ ("Ronaspheres") are advantageous, which are marketed by Merck and are suitable especially for the optical reduction of fine wrinkles.

It can additionally be advantageous to dispense with a substrate such as mica entirely. Particular preference is given to iron pearl lustre pigments which are prepared without the use of mica. Such pigments are obtainable, for example, under the trade name Sicopearl Kupfer 1000 from BASF.

Also particularly advantageous are effect pigments, which are obtainable from Flora Tech under the trade name Metasomes Standard/Glitter in various colours (yellow, red, green, blue). The glitter particles are in mixtures with various auxiliary substances and colourings (such as, for example, the colourings having the Colour Index (CI) numbers 19140, 77007, 77289, 77491).

The colourings and pigments can be present either individually or in a mixture and may be mutually coated, different colour effects generally being produced by different coating thicknesses. The total amount of colourings and colour-giving pigments is advantageously selected from the range of, for example, from 0.1 wt. % to 30 wt. %, preferably from 0.5 to 15 wt. %, especially from 1.0 to 10 wt. %, in each case based on the total weight of the preparations.

It is also advantageous within the scope of the present invention to produce cosmetic and dermatological preparations whose principal purpose is not to protect against sunlight but which nevertheless have a content of further UV-protecting substances. For example, UV-A or UV-B filtering substances are usually incorporated into day creams or make-up products. UV-protecting substances, like antioxidants and, if desired, preservatives, also effectively protect the preparations themselves against spoiling. Also advantageous are cosmetic and dermatological preparations in the form of a sun protection agent.

Accordingly, the preparations within the scope of the present invention preferably comprise at least one further UV-A, UV-B and/or broad-band filter substance. The formulations may, although it is not necessary, optionally also comprise one or more organic and/or inorganic pigments are UV filter substances, which pigments may be present in the water phase and/or the oil phase.

The preparations according to the present invention may advantageously also be in the form of so-called oil-free cosmetic or dermatological emulsions, which comprise a water phase and, as a further phase, at least one UV filter substance that is liquid at room temperature, and which, in particular, may advantageously be free of further oil components.

Particularly advantageous UV filter substances within the scope of the present invention that are liquid at room temperature are homomenthyl salicylate (INCI: homosalate), 2-ethylhexyl 2-cyano-3,3-diphenylacrylate (INCI: octocrylene), 2-ethylhexyl 2-hydroxybenzoate (2-ethylhexyl salicylate, octyl salicylate, INCI: ethylhexyl salicylate) and esters of cinnamic acid, preferably 4-methoxycinnamic acid (2-ethylhexyl) esters (2-ethylhexyl 4-methoxycinnamate, INCI: ethylhexyl methoxycinnamate) and 4-methoxycinnamic acid isopentyl ester (isopentyl-4-methoxycinnamate, INCI: isoamyl p-methoxycinnamate), 3-(4-(2,2-bis ethoxycarbonylvinyl)-phenoxy)propenyl)-methoxysiloxane/dimethylsiloxane copolymer, which is obtainable, for example, under the trade name Parsol® SLX from Hoffmann La Roche.

Preferred inorganic pigments are metal oxides and/or other metal compounds that are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and blends of such oxides, as well as the sulfate of barium ($BaSO_4$).

Within the scope of the present invention, the pigments may advantageously also be used in the form of commercially available oily or aqueous pre-dispersions. Dispersing aids and/or solubilisers may advantageously be added to such pre-dispersions.

According to the invention, the pigments may advantageously be surface-treated ("coated"), whereby a hydrophilic, amphiphilic or hydrophobic nature, for example, is to be formed or retained. This surface treatment may consist in providing the pigments with a thin hydrophilic and/or hydrophobic inorganic and/or organic layer by processes known per se. The various surface coatings may also comprise water within the scope of the present invention.

Inorganic surface coatings within the scope of the present invention may consist of aluminium oxide ($Al_2O_3$), aluminium hydroxide $Al(OH)_3$, or aluminium oxide hydrate (also: alumina, CAS No.: 1333-84-2), sodium hexametaphosphate $(NaPO_3)6$, sodium metaphosphate $(NaPO_3)_n$, silicon dioxide ($SiO_2$) (also: silica, CAS No.: 7631-86-9) or iron oxide ($Fe_2O_3$). The inorganic surface coatings may occur alone, in combination and/or in combination with organic coating materials.

Organic surface coatings within the scope of the present invention may consist of vegetable or animal aluminium stearate, vegetable or animal stearic acid, lauric acid, dimethylpolysiloxane (also: dimethicone), methylpolysiloxane (methicone), simethicone (a mixture of dimethylpolysiloxane having an average chain length of from 200 to 350 dimethylsiloxane units, and silica gel) or alginic acid. These organic surface coatings may occur alone, in combination and/or in combination with inorganic coating materials. Zinc oxide particles and pre-dispersions of zinc oxide particles that are suitable according to the invention are obtainable under the following trade names from the listed companies:

| Trade name | Coating | Manufacturer |
| --- | --- | --- |
| Z-Cote HP 1 | 2% dimethicone | BASF |
| Z-Cote | / | BASF |
| ZnO NDM | 5% dimethicone | H & R |
| MZ-303S | 3% methicone | Tayca Corporation |
| MZ-505S | 5% methicone | Tayca Corporation |

Suitable titanium dioxide particles and pre-dispersions of titanium dioxide particles are obtainable under the following trade names from the listed companies:

| Trade name | Coating | Manufacturer |
| --- | --- | --- |
| MT-100TV | aluminium hydroxide/ stearic acid | Tayca Corporation |
| MT-100Z | aluminium hydroxide/ stearic acid | Tayca Corporation |
| Eusolex T-2000 | alumina/simethi cone | Merck KgaA |
| Titandioxid T805 (Uvinul $TiO_2$) | octyltrimethoxy-silane | Degussa |
| Tioveil AQ 10PG | alumina/silica | Solaveil/Uniquema |
| Eurolex T-aqua | water/alumina/ sodium metaphosphate | Merck |

Further advantageous pigments are latex particles. Latex particles that are advantageous according to the invention are those described in the following publications: U.S. Pat. No. 5,663,213 or EP 0 761 201. Particularly advantageous latex particles are those which can be formed from water and styrene/acrylate copolymers and which are obtainable, for example, under the trade name "Alliance SunSphere" from Rohm & Haas.

Advantageous UV-A filter substances within the scope of the present invention are dibenzoylmethane derivatives, in particular 4-(tert.-butyl)-4'-methoxydibenzoylmethane (CAS No. 70356-09-1), which is marketed by Givaudan under the trade mark Parsol™ 1789 and by Merck under the trade name Eusolex ™ 9020.

Advantageous further UV filter substances within the scope of the present invention are sulfonated, water-soluble UV filters, such as, for example:
phenylene-1,4-bis-(2-benzimidazyl)-3,3'-5,5'-tetrasulfonic acid and its salts, particularly the corresponding sodium, potassium or triethanolammonium salts, in particular the phenylene-1,4-bis-(2-benzimidazyl)-3,3'-5,5'-tetrasulfonic acid bis-sodium salt having the INCI name disodium phenyl dibenzimidazol tetrasulfonate (CAS No.: 180898-37-7), which is obtainable, for example, under the trade name Neo Heliopan AP from Haarmann & Reimer;
salts of 2-phenylbenzimidazole-5-sulfonic acid, such as its sodium, potassium or triethanolammonium salt as well as sulfonic acid itself having the INCI name phenylbenzimidazole sulfonic acid (CAS No. 27503-81-7), which is obtainable, for example, under the trade name Eusolex 232 from Merck or under the trade name Neo Heliopan Hydro from Haarmann & Reimer;

1,4-di(2-oxo-10-sulfo-3-bornylidenemethyl)-benzene (also: 3,3'-(1,4-phenylenedimethylene)-bis-(7,7-dimethyl-2-oxo-bicyclo-[2.2.1]hept-1-ylmethane sulfonic acid) and its salts (especially the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name terephtalidene dicampher sulfonic acid (CAS No.: 90457-82-2) and is obtainable, for example, under the trade name Mexoryl SX from Chimex;

sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl) sulfonic acid and their salts.

Advantageous UV filter substances within the scope of the present invention are also benzoxazole derivatives, which are distinguished by the following structural formula

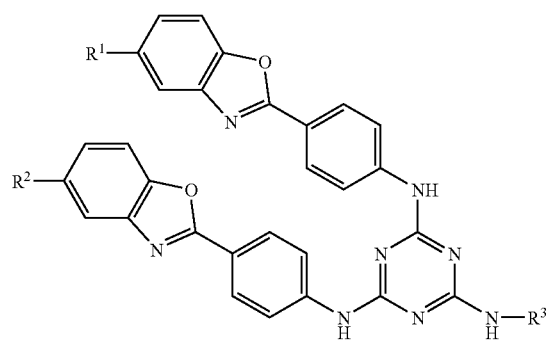

wherein $R^1$, $R^2$ and $R^3$, independently of one another, are selected from the group of the branched or unbranched, saturated or unsaturated alkyl radicals having from 1 to 10 carbon atoms. It is particularly advantageous according to the invention to choose the radicals $R^1$ and $R^2$ to be identical, in particular from the group of the branched alkyl radicals having from 3 to 5 carbon atoms. It is also particularly advantageous within the scope of the present invention if $R^3$ represents an unbranched or branched alkyl radical having 8 carbon atoms, in particular the 2-ethylhexyl radical.

The benzoxazole derivative that is particularly preferred according to the invention is 2,4-bis-[5-1(dimethylpropyl)-benzoxazol-2-yl-(4-phenyl)-imino]-6-(2-ethylhexyl)-imino-1,3,5-triazine having the CAS No. 288254-16-0, which is distinguished by the structural formula:

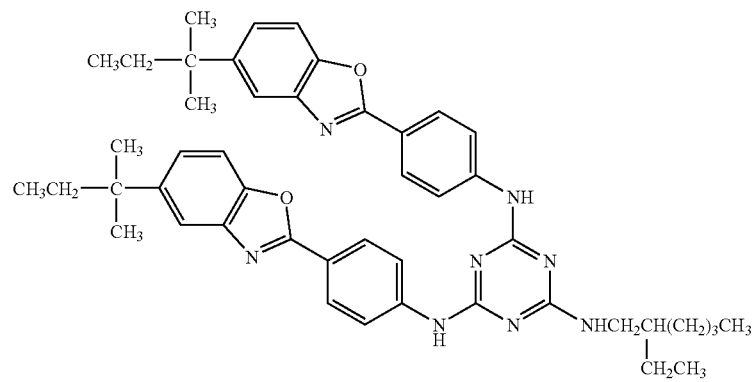

and is obtainable from 3V Sigma under the trade name Uvasorb™ K2A.

The benzoxazole derivative(s) is/are advantageously in dissolved form in the cosmetic preparations according to the invention. However, it may also be advantageous for the benzoxazole derivative(s) to be present in pigment form, that is to say undissolved form—for example in particle sizes of from 10 nm to 300 nm.

Further advantageous UV filter substances within the scope of the present invention are so-called hydroxybenzophenones. Hydroxybenzophenones are distinguished by the following structural formula:

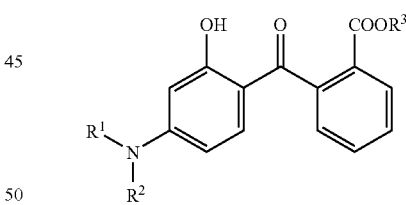

wherein $R^1$ and $R^2$, independently of one another, represent hydrogen, $C_1$-$C_{20}$-alkyl, $C_3$-$C_{10}$-cycloalkyl or $C_3$-$C_{10}$-cycloalkenyl, wherein the substituents $R^1$ and $R^2$, together with the nitrogen atom to which they are bonded, may form a 5- or 6-membered ring, and $R^3$ represents a $C_1$-$C_{20}$-alkyl radical.

A particularly advantageous hydroxybenzophenone within the scope of the present invention is 2-(4'-diethylamino-2'-hydroxybenzoyl)-benzoic acid hexyl ester (also: aminobenzophenone), which is distinguished by the following structure:

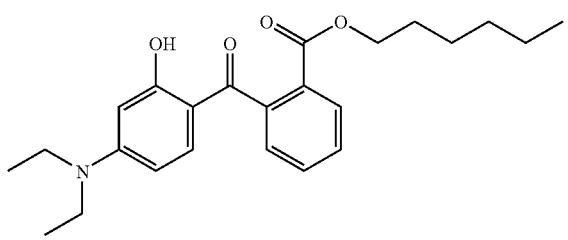

and is obtainable under Uvinul A Plus from BASF.

Advantageous UV filter substances within the scope of the present invention are also so-called broad-band filters, that is to say, filter substances which absorb both UV-A and UV-B radiation. Advantageous broad-band filters or UV-B filter substances are, for example, triazine derivatives, such as, for example, 2,4-bis-[4-(2-ethyl-hexyloxy)-2-hydroxy]-phenyl-6-(4-methoxyphenyl)-1,3,5-triazine (INCI: bis-ethylhexyloxyl-phenol methoxyphenyl triazine), which is obtainable under the trade name Tinosorb™ S from CIBA-Chemikalien GmbH;

dioctylbutylamidotriazone (INCI: diethylhexyl butamido triazone), which is obtainable under the trade name UVA-SORB HEB from Sigma 3 V;

4,4',4"-(1,3,5-triazine-2,4,6-triyltriamino)-tris-benzoic acid tris(2-ethylhexyl ester), also: 2,4,6-tris-[anilino-(p-carbo-2'-ethyl-1'-hexyloxy)]-1,3,5-triazine (INCI: ethylhexyl triazone), which is marketed by BASF Aktiengesellschaft under the trade mark UVINUL™ T 150;

2-[4,6-bis(2,4-dimethylphenyl)-1,3,5-triazin-2-yl]-5-(octyloxy)phenol (CAS No.: 2725-22-6).

An advantageous broad-band filter within the scope of the present invention is also 2,2-methylene-bis-(6-(2H-benzotriazol-2-yl)-4-(1,1,3,3-tetramethylbutyl)-phenol)(INCI: methylene bis-benztriazolyl tetramethylbutylphenol), which is obtainable, for example, under the trade name Tinosorb™ M from CIBA-Chemikalien GmbH. Another advantageous broad-band filter within the scope of the present invention is also 2-(2H-benzotriazol-2-yl)-4-methyl-6-[2-methyl-3-[1,3,3,3-tetramethyl-1-[(trimethylsilyl)oxy]disiloxanyl]propyl]-phenol (CAS No.: 155633-54-8) having the INCI name drometrizole trisiloxane.

The further UV filter substances may be oil-soluble or water-soluble. Advantageous oil-soluble filter substances are, for example:

3-benzylidenecamphor derivatives, preferably 3-(4-methylbenzylidene)camphor, 3-benzylidenecamphor;

4-aminobenzoic acid derivatives, preferably 4-(dimethylamino)-benzoic acid (2-ethylhexyl) ester, 4-(dimethylamino)benzoic acid amyl ester;

2,4,6-trianilino-(p-carbo-2'-ethyl-1'-hexyloxy)-1,3,5-triazine;

esters of benzalmalonic acid, preferably 4-methoxybenzalmalonic acid di(2-ethylhexyl) ester;

esters of cinnamic acid, preferably 4-methoxycinnamic acid (2-ethylhexyl) ester, 4-methoxycinnamic acid isopentyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Advantageous water-soluble filter substances are, for example: sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and their salts.

A further light protection filter substance that can advantageously be used according to the invention is ethylhexyl-2-cyano-3,3-diphenylacrylate (octocrylene), which is obtainable from BASF under the name Uvinul® N 539 T.

Particularly advantageous preparations within the scope of the present invention that are distinguished by high or very high UV-A protection preferably comprise, in addition to the filter substance(s) according to the invention, also further UV-A and/or broad-band filters, in particular dibenzoylmethane derivatives [for example 4-(tert.-butyl)-4'-methoxydibenzoylmethane] and/or 2,4-bis-[4-(2-ethylhexyloxy)-2-hydroxy]-phenyl-6-(4-methoxyphenyl)-1,3,5-triazine and/or phenylene-1,4-bis-(2-benzimidazyl)-3,3'-5,5'-tetrasulfonic acid bis-sodium salt, in each case individually or in any desired combinations with one another.

The list of the mentioned UV filters which can be used within the scope of the present invention is, of course, not intended to be limiting.

The preparations according to the present invention advantageously comprise the substances that absorb UV radiation in the UV-A and/or UV-B range in a total amount of, for example, from 0.1 wt. % to 30 wt. %, preferably from 0.5 to 20 wt. %, especially from 1.0 to 15.0 wt. %, in each case based on the total weight of the preparations, in order to provide cosmetic preparations which protect the hair or the skin from the entire range of ultraviolet radiation.

The preparations within the scope of the present invention may advantageously also comprise further substances which increase the hygrostability of the products. Examples of advantageous substances of this type are water-soluble or water-dispersible polyoxyethylene-polyoxypropylene block polymers (CTFA name: polaxamers, CAS No. 9003-11-6) having the following structure:

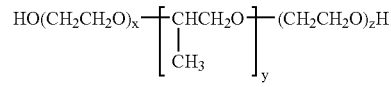

wherein x, y and z represent integers from the range from 2 to 130, especially from 15 to 100, and x and z are identical but are chosen independently of y. Among these, there can be used particularly advantageously polaxamer 188 [wherein x=75, y=30 and z=75], which is obtainable under the trade name Lutrol F 68 (alt: Pluronic F 68) from BASF, polyxamer 185 [wherein x=19, y=30 and z=19] (Lubrajel WA from ISP), polyxamer 235 [wherein x=27, y=39 and z=27] (Pluronic F 85 from BASF) and/or polyxamer 238 [wherein x=97, y=39 and z=97] (Pluronic F 88 from BASF).

Further advantageous substances which can contribute towards increasing the hygrostability but are incorporated into the oil phase of the preparations according to the present invention are particular wax components, such as acetylated glycol stearate with tristearin (e.g. Unitwix from ISP with INCI: acetylated glycol stearate and tristearin), C18-36 fatty acid triglyceride (e.g. Syncrowax HGLC from Crode GmbH with INCI: C18-36 acid triglyceride) and also the substances obtainable under the trade names "Perfroma V 825" (synthetic wax) from New Phase Technologies, as well as PEG-45 dodecyl glycol copolymer (INCI: PEG-45 dodecyl glycol copolymer), PEG-22 dodecyl glycol copolymer (INCI: PEG-22 dodecyl glycol copolymer), methoxy PEG-22 dodecyl glycol copolymer (INCI: methoxy PEG-22 dodecyl glycol copolymer), which are obtainable from AKZO Nobel.

It is particularly advantageous within the scope of the present invention to combine the polymers used according to the invention with one or more of the mentioned substances, in order to improve the hygrostability of the preparations still further.

The Examples which follow are intended to illustrate the present invention without limiting it. The numerical values in the Examples mean percent by weight, based on the total weight of the preparations in question. The sun protection formulations according to the invention can comprise as filler granulated pyrogenically prepared silicon dioxide according to DE 0153077. In sun protection formulations, the surface-modified pyrogenically prepared titanium dioxide mixed oxides according to the invention exhibit improved transparency, increased transmission at 380 nm and accordingly reduced whitewashing, as well as a reduced thickening action. It is possible to prepare dispersions having an increased degree of filling.

EXAMPLES

1. Surface Modification

As starting material there are used pyrogenically prepared silicon dioxide-titanium dioxide mixed oxides, which are prepared according to WO 2004/056927. The physicochemical data of the starting materials are shown in Table 1.

TABLE 1

| Oxide | Specific surface area according to BET [$m^2/g$] | $SiO_2$ content [%] | $TiO_2$ content [%] | Tamped density [g/l] | pH value |
|---|---|---|---|---|---|
| 1 | 67 | 7.0 | 93.0 | 56 | 3.8 |
| 2 | 57 | 2.1 | 97.9 | 65 | 4.2 |
| 3 | 62 | 3.8 | 96.2 | 66 | 4.0 |
| 4 | 105 | 7.2 | 92.8 | 46 | 3.7 |
| 5 | 63 | 8.2 | 91.8 | 51 | 3.6 |
| 6 | 59 | 12.7 | 87.3 | 58 | 3.8 |

Tetraethoxysilane (TEOS) is used as the surface-modifying agent. The pyrogenically prepared silicon dioxide-titanium dioxide mixed oxide is placed in a mixer, sprayed with water and then sprayed with the surface-modifying agent TEOS. The mixture is then tempered. The details are given in Table 2.

TABLE 2

| Name | Oxide* | SM** | Parts SM**/ 100 parts oxide | Parts $H_2O$***/ 100 parts oxide | Tempering temperature [° C.] | Tempering time [h] | Grinding |
|---|---|---|---|---|---|---|---|
| Example 1 | 1 | TEOS | 20 | 5 | 130 | 3 | no |
| Example 2 | 2 | TEOS | 27.5 | 5 | 130 | 3 | no |
| Example 3 | 2 | TEOS | 50 | 5 | 130 | 3 | no |
| Example 4 | 3 | TEOS | 21.6 | 5 | 130 | 3 | no |
| Example 5 | 3 | TEOS | 39 | 5 | 130 | 3 | no |
| Example 6 | 1 | TEOS | 8 | 5 | 130 | 3 | no |
| Example 7 | 1 | TEOS | 25.5 | 5 | 130 | 3 | no |
| Example 8 | 4 | TEOS | 50 | 5 | 130 | 3 | no |
| Example 9 | 4 | TEOS | 56 | 5 | 130 | 3 | no |
| Example 10 | 4 | TEOS | 34 | 5 | 130 | 3 | no |
| Example 11 | 4 | TEOS | 17 | 5 | 130 | 3 | no |
| Example 12 | 5 | TEOS | 56 | 5 | 130 | 3 | no |
| Example 13 | 5 | TEOS | 34 | 5 | 130 | 3 | no |
| Example 14 | 5 | TEOS | 17 | 5 | 130 | 3 | no |
| Example 15 | 6 | TEOS | 56 | 5 | 130 | 3 | no |
| Example 16 | 6 | TEOS | 34 | 5 | 130 | 3 | no |
| Example 17 | 6 | TEOS | 17 | 5 | 130 | 3 | no |

*see Table under 7. (*: 1 = PS 8; 2 = PS 2; 3 = PS 4; 4 = VP 3946; 5 = VP 3950; 6 = VP 3962)

**SM = surface-modifying reagent, TEOS = tetraethoxysilane

***0.5% aqueous ammonia solution was used instead of $H_2O$

The physico-chemical data of the surface-modified silicon dioxide-titanium dioxide mixed oxides are shown in Table 3.

TABLE 3

| Name | Spec. surface area acc. to BET [m²/g] | Tamped density [g/l] | Loss on drying [%] | Ignition loss [%] | C content [%] | pH value | SiO₂ content (total) [%] | SiO₂ content by SM* [%] |
|---|---|---|---|---|---|---|---|---|
| Example 1 | 77 | 97 | 0.6 | 2.0 | — | 4.0 | 11.4 | 4.4 |
| Example 2 | 67 | 112 | 1.6 | 1.5 | 0.4 | 3.8 | 8.1 | 6.0 |
| Example 3 | 74 | 137 | 2.3 | 1.8 | 0.3 | 3.9 | 10.4 | 8.3 |
| Example 4 | 74 | 111 | 1.0 | 1.6 | 0.4 | 3.7 | 8.6 | 4.8 |
| Example 5 | 84 | 123 | 2.8 | 1.6 | 0.4 | 3.9 | 11.8 | 8.0 |
| Example 6 | 67 | 73 | 1.7 | 1.2 | 0.2 | 3.7 | 8.7 | 1.7 |
| Example 7 | 84 | 94 | 2.4 | 1.8 | 0.4 | 3.8 | 12.2 | 5.2 |
| Example 8 | 120 | 100 | 0.8 | 4.3 | 2.4 | 3.3 | 15.6 | 8.4 |
| Example 9 | 114 | 109 | 1.1 | 3.9 | 2.1 | 3.3 | 16.5 | 9.3 |
| Example 10 | 118 | 86 | 1.8 | 2.9 | 1.2 | 3.8 | 14.9 | 7.7 |
| Example 11 | 110 | 71 | 0.5 | 2.2 | 0.75 | 3.8 | 11.4 | 4.2 |
| Example 12 | 75 | 132 | 0.8 | 3 | 1.6 | 4.3 | 14.6 | 6.4 |
| Example 13 | 77 | 102 | 1.1 | 2.5 | 1.5 | 4.1 | 14.6 | 6.4 |
| Example 14 | 73 | 83 | 0.2 | 1.9 | 0.75 | 4.2 | 12.2 | 4.0 |
| Example 15 | 64 | 142 | 0.4 | 3.2 | 1.5 | 4.5 | 20.7 | 8.0 |
| Example 16 | 72 | 100 | 0.8 | 4.3 | 2.4 | 3.3 | 19.1 | 6.4 |
| Example 17 | 72 | 89 | 1.2 | 2.0 | 0.9 | 4.7 | 17.2 | 4.5 |

SM* = surface modification

2. Sun Protection Formulations

Test Methods

The materials according to Examples 8, 11, 12 and 15 are dispersed and the transparency and viscosity are tested using the following methods.

Preparation of the Dispersion 278.25 g of TEGOSOFT® TN are placed in a 500 ml PE beaker, and 21.75 g of the titanium dioxide powder to be tested are stirred in with the aid of a dissolver (Pendraulik type LM34 No. 29490, disk diameter 6 cm) at 470 rpm, and dispersion is then carried out for five minutes at 3000 rpm. The dispersion is then dispersed for two minutes at 15,000 rpm using an Ultra-Turrax stirrer (Polytron PT3100, dispersing tool PT-DA 3020/2 EC). Finally, the dispersion is dispersed for a further five minutes in a water-cooled container using the Ultra-Turrax stirrer at 15,000 rpm, the PT-DA 3030-6060/3 EC dispersing tool now being used.

Transparency (T ΔL*)

The transparency of the 7.25 wt. % dispersions is determined using a Data Color SF600 Plus spectrophotometer. The dispersions are applied by means of a 12 μm spiral blade to lacquered black cardboard using an Erichsen Testing Equipment K Control Coater application device, application speed 2.

Three measuring points are measured per application. The mean of these 3 measurements is calculated. To protect the device, measurement is carried out with a distance ring. The calculation is carried out using the CIE-L*a*b* system, light type D65/10°. The device is calibrated using a black standard BHB SF600, hollow block and a white standard no. 3138. The Δ L* value corresponds to the luminosity or transparency of the dispersion. This value is calculated from the mean value that was determined minus the value of the black cardboard. The L value of the lacquered black cardboard is about L* value=8. The lower the Δ L* value, the more transparent the dispersion.

UV-Vis Spectra (TM320 and 380 nm)

The UV-Vis spectra of 3 wt. % dispersions are measured in a 10 μm quartz glass cuvette, which can be taken apart, using a Specord 200 UV-Vis spectrophotometer having a photometer sphere (Analytik Jena AG). To this end, the above-described oily dispersions are diluted with Tego-soft TN. While stirring with the dissolver (Pendraulik type LM34 No. 29490, disk diameter 5 cm; 1000-4000 rpm), AEROSIL® 200 is then added in portions in order to prepare a gel-like composition and to stabilise the oxide. After the last addition of AEROSIL, dispersion must be continued for at least 2 minutes in order to ensure homogeneous distribution of the AEROSIL. As result, the transmission (%) in the range of 290-500 nm is obtained.

Viscosity (V)

The viscosity is determined using a Brookfield rheometer RVDV-III+cP. The measurement is carried out in a PE mixing beaker (350 ml) with the RV spindle set, at 10 rpm. After one minute, the value is read off in mPas.

Results

Characterisation of surface- and structure-modified pyrogenically prepared titanium dioxides and titanium-iron mixed oxides Examples 8, 11, 12 and 15

| Name | Transparency (TΔL*) | Transmission 320 nm (%) | Transmission 380 nm (%) | Viscosity (mPas) |
|---|---|---|---|---|
| Comparison example AEROXIDE TiO₂ T805 | 15 | 2 | 9 | 628 |
| Example 8 | 3 | 10 | 43 | 61 |
| Example 11 | 2 | 6 | 37 | 222 |
| Example 12 | 8 | 9 | 24 | 36 |
| Example 15 | 9 | 12 | 27 | 32 |

Advantages of the products of Examples 8, 11, 12 and 15 over the comparison example AEROXIDE TiO2 T 805 are:

improved transparency increased transmission at 380 nm and accordingly reduced whitewashing reduced thickening action. This permits the preparation of highly filled dispersions.

Sun Protection Formulations 1

| | % | Constituent | |
|---|---|---|---|
| A. | 3.00 | Isopropyl myristate | Isopropyl myristate |
| | 8.00 | Jojoba oil | Simmondsia Chinensis (Jojoba) seed oil |
| | 4.00 | Uvinul ® MC 80 | Octyl methoxycinnamate |
| | 1.00 | Abil ® 350 | Dimethicone |
| | 6.00 | Cremophor ® WO 7 | PEG-7 hydrogenated castor oil |
| | 2.00 | Ganex ® V 216 | PVP/hexadecene copolymer |
| | 2.00 | Elfacos ® ST 9 | PEG-45/dodecyl glycol copolymer |
| | 2.00 | Uvinul ® MBC 95 | 4-Methylbenzylidene camphor |
| B | 3.00 | Finely divided titanium dioxide | Titanium dioxide (and) tetraethyl orthosilicate |
| | 5.00 | Z-Cote ® HP 1 | Zinc oxide (and) dimethicone |
| C | 1.00 | Magnesium sulfate-7-hydrate | Magnesium sulfate |
| | 5.00 | Glycerol 87% | Glycerol |
| | 0.20 | Edeta ® BD | Disodium EDTA |
| | 0.30 | Germoll ® 115 | Imidazolidinyl urea |
| | 57.00 | Water dem. | Water |
| | q.s. | Perfume | |
| | 0.50 | Euxyl ® K3000 | Phenoxyethanol, methylparaben, butylparaben, ethylparaben, propylparaben, isobutylparaben |

Phase A is heated to 80° C. and phase B is added. The mixture is then homogenised for 3 minutes Phase C is heated to 80° C. and stirred into the mixture of phases A and B. Homogenisation is thereby carried out.

Sun Protection Formulation 2

| | % | Constituent | |
|---|---|---|---|
| A. | 6.00 | Cremophor ® WO 7 | PEG-7 hydrogenated castor oil |
| | 2.00 | Elfacos ® ST 9 | PEG-45/dodecyl glycol copolymer |
| | 3.00 | Isopropyl myristate | Isopropyl myristate |
| | 8.00 | Jojoba oil | Jojoba (Buxus Chinensis) oil |
| | 4.00 | Uvinul ® MC 80 | Octyl methoxycinnamate |
| | 2.00 | Uvinul ® MBC 95 | 4-Methylbenzylidene camphor |
| | 3.00 | Finely divided titanium dioxide | Titanium dioxide (and) tetraethyl orthosilicate |
| | 1.00 | Abil ® 350 | Dimethicone |
| | 5.00 | Z-Cote ® HP 1 | Zinc oxide, dimethicone |
| B | 0.20 | Edeta ® BD | Disodium EDTA |
| | 5.00 | Glycerol 87% | Glycerol |
| | q.s. | Preservative | |
| | 60.80 | Water dem. | Aqua dem. |
| C | q.s. | Perfume | |

Phases A and B are heated separately to 85° C. Phase B is stirred into phase A, and the mixture is homogenised. The mixture is cooled to 40° C., phase C is added and the mixture is then homogenised.

Results

| | Formulation 1 Transparency | Formulation 2 Transparency |
|---|---|---|
| Comparison example AEROXIDE TiO₂ T805 | not satisfactory | not satisfactory |
| Example 8 | very good | very good |
| Example 11 | very good | very good |
| Example 12 | good | good |
| Example 15 | good | good |

All references cited herein are fully incorporated by reference. Having now fully described the invention, it will be understood by one of ordinary skill in the art that the invention may be performed within a wide and equivalent range of conditions, parameters and the like, without affecting the spirit or scope of the invention or any embodiment thereof.

What is claimed is:

1. Pyrogenically prepared surface-modified silicon dioxide-titanium dioxide mixed oxides produced by a process comprising modifying the surface of pyrogenically prepared silicon dioxide-titanium dioxide mixed oxides with a silica or organosilane surface-modifying agent of formula I or a silane formed by the partial hydrolysis and condensation of an organosilane of formula I:

$$Si(OR)_x(OR')_y(OR'')_u(OR''')_v \qquad (I)$$

wherein:

$x=0,1,2,3,4$ $y=0,1,2,3,4$ $u=0,1,2,3,4$ $v=0,1,2,3,4$ $x+y+u+v=4$ and

R, R', R" and R'" are each independently a $C_1$-$C_6$ alkyl.

2. The pyrogenically prepared surface-modified silicon dioxide-titanium dioxide mixed oxides of claim 1, wherein R, R', R" and R'" are each independently a $C_1$-$C_3$ alkyl.

3. A process for the preparation of pyrogenically prepared, surface-modified silicon dioxide-titanium dioxide mixed oxides according to claim 1, comprising:

a) surface modifying pyrogenically prepared silicon dioxide-titanium dioxide mixed oxides by spraying said pyrogenically prepared silicon dioxide-titanium dioxide mixed oxides with a surface-modifying agent; and b) tempering the surface modified silicon dioxide-titanium dioxide mixed oxides of step a).

4. The process of claim 3, wherein the surface modification of said pyrogenically prepared silicon dioxide-titanium dioxide mixed oxides in step a) takes place in a mixer.

5. The process of claim 3, wherein, prior to spraying said pyrogenically prepared silicon dioxide-titanium dioxides with said surface-modifying agent in step a), said pyrogenically prepared silicon dioxide-titanium dioxides are sprayed with water.

6. The process of claim 3, wherein, prior to tempering the surface modified pyrogenically prepared silicon dioxide-titanium dioxide mixed oxides in step b), said surface modified pyrogenically prepared silicon dioxide-titanium dioxide mixed oxides are mixed together in a mixer.

7. The process of claim 3, wherein R, R', R" and R'" are each independently a $C_1$-$C_3$ alkyl.

8. The process of claim 7, wherein said tempering in step b) comprises heating said surface modified silicon dioxide-titanium dioxide mixed oxides at a temperature of 20-400° C. for a period of 0.1-6 hours.

9. The process of claim 8, wherein said heating is carried out under an inert, protecting gas.

10. The process of claim 9, wherein said gas is nitrogen.

11. A sun protection agent, comprising from 0.1 to 25 wt % of a surface-modified, pyrogenically prepared silicon dioxide-titanium dioxide mixed oxide according to claim 1.

12. The sun protection agent of claim 11, wherein said sun protection agent comprises a water phase and an oil phase.

13. The sun protection agent of claim 12, wherein:
a) said water phase comprises said surface-modified, pyrogenically prepared silicon dioxide-titanium dioxide mixed oxide; and
b) said oil phase comprises a hydrophobic metal oxide.

14. A process for the preparation of a pyrogenically prepared, surface-modified silicon dioxide-titanium dioxide mixed oxides, comprising:
a) treating pyrogenically prepared silicon dioxide-titanium dioxide mixed oxides with a surface-modifying agent in vapour form and
b) heat treating the pyrogenically prepared silicon dioxide-titanium dioxide mixed oxides that have been surface modified in step a)

wherein said surface modifying agent comprises a silica or organosilane surface-modifying agent of formula I or a silane formed by the partial hydrolysis and condensation of an organosilane of formula I:

$$\text{Si}(OR)_x(OR')_y(OR'')_u(OR''')_v \quad (I)$$

wherein:
$x=0,1,2,3,4$
$y=0,1,2,3,4$
$u=0,1,2,3,4$
$v=0,1,2,3,4$
$x+y+u+v=4$ and
R, R', R" and R''' are each independently a $C_1$-$C_6$ alkyl.

15. The process of claim 14, wherein R, R', R" and R''' are each independently a $C_1$-$C_3$ alkyl.

16. The process of claim 15, wherein said heat treating of step b) takes place at a temperature of 50-800° C. for a period of 0.1-6 hours.

17. The process of claim 16, wherein said heat treating takes place under an inert, protecting gas.

* * * * *